United States Patent [19]

Makovec et al.

[11] Patent Number: 5,723,494

[45] Date of Patent: Mar. 3, 1998

[54] DERIVATIVES OF GLUTAMIC AND ASPARTIC ACIDS, A METHOD OF PREPARING THEM, AND THEIR USE AS DRUGS FOR ENHANCING MEMORY AND LEARNING

[75] Inventors: Francesco Makovec, Monza; Walter Peris, Milan; Lucio C. Rovati; Luigi A. Rovati, both of Monza, all of Italy

[73] Assignee: Rotta Research Laboratorium S.P.A., Milan, Italy

[21] Appl. No.: 513,964

[22] PCT Filed: Mar. 2, 1994

[86] PCT No.: PCT/EP94/00604

§ 371 Date: Sep. 11, 1995

§ 102(e) Date: Sep. 11, 1995

[87] PCT Pub. No.: WO94/20454

PCT Pub. Date: Sep. 15, 1994

[30] Foreign Application Priority Data

Mar. 10, 1993 [IT] Italy ................... TO93A0167

[51] Int. Cl.$^6$ ............... C07C 237/06; C07C 237/24; A61K 31/16; A61K 31/435

[52] U.S. Cl. ............. 514/563; 562/499; 562/500; 562/501

[58] Field of Search ............... 562/499, 500, 562/501

[56] References Cited

FOREIGN PATENT DOCUMENTS

WO 92/10479  6/1992  WIPO.

OTHER PUBLICATIONS

Francesco Makovec et al. Structure—Antigastrin Activity Relationships of New (R)-4-Benzamido-5-oxopentanoic Acid Derivatives. J. Med. Chem. 1992, 35, 28-38.

Primary Examiner—Mukund J. Shah
Assistant Examiner—Bruck Kifle
Attorney, Agent, or Firm—Sughrue, Mion, Zinn, Macpeak & Seas, PLLC

[57] ABSTRACT

Compounds represented by general formula (I) and (II), in which r is 1 or 2, $R_2$ and $R_3$ are selected independently from H, $CH_3$, $C_2H_5$ and CHO, provided that $R_2$ and $R_3$ are not simultaneously CHO, and in which $R_1$ is selected from: an aminoalkyl adamantyl group, a monocyclic aminoalkyl group, a dicyclic aminospiro group, a dicyclic amino group (orthofused), a dicyclic amino group, and azacycloalkyl group, an azadicyclic group (orthofused), a dicyclic azaspiro group, and azadicyclic group, and azacycloalkyl group, and a linear or branched aminoalkyl group.

11 Claims, No Drawings

DERIVATIVES OF GLUTAMIC AND ASPARTIC ACIDS, A METHOD OF PREPARING THEM, AND THEIR USE AS DRUGS FOR ENHANCING MEMORY AND LEARNING

The subject of the present invention is derivatives of glutamic and aspartic acids which have memory- and learning-enhancing activity and can be represented by the general formulae indicated below:

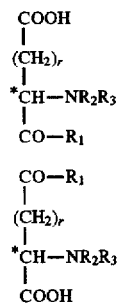

(I)

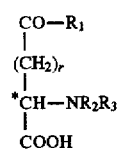

(II)

in which r is 1 or 2, $R_2$ and $R_3$ are selected independently from H, $CH_3$, $C_2H_5$ and CHO, provided that $R_2$ and $R_3$ are not simultaneously CHO, and in which $R_1$ is selected from:

1) an aminoalkyl adamantyl group represented by:

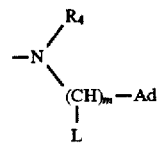

in which $R_4$ is H or $C_1$–$C_5$ alkyl or alkoxyalkyl, m is a whole number between 0 and 3, L is H or $C_1$–$C_3$ alkyl or alkoxyalky and Ad is adamantyl (1- or 2-yl);

2) a monocyclic aminoalkyl group represented by:

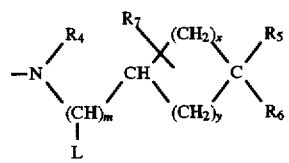

in which $R_4$, m and L have the meanings given above, x and y are selected independently and may have values of between 1 and 4, provided that the ring formed comprises between 5 and 10 carbon atoms; $R_5$, $R_6$ and $R_7$ are selected independently from H and a $C_1$–$C_4$ alkyl or alkoxyalkyl group;

3) a dicyclic aminospiro group represented by:

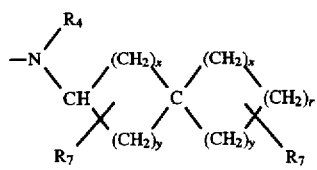

in which $R_4$, $R_7$, r, x and y have the meanings given above;

4) a dicyclic amine group (orthofused) represented by:

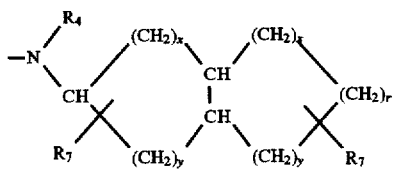

in which $R_4$, $R_7$, r, x and y have the meanings given above;

5) a dicyclic amino group represented by:

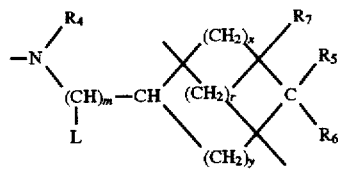

in which $R_4$, $R_5$, $R_6$, $R_7$, L, m, r, x and y have the meanings given above.

6) an azacycloalkyl group represented by:

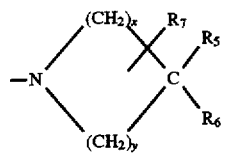

in which $R_5$, $R_6$, $R_7$, x and y have the meanings given above.

7) an azadicyclic group (orthofused) represented by:

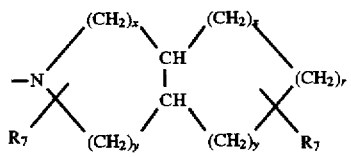

in which $R_7$, r, x, and y have the meanings given above;

8) a dicyclic azaspiro group represented by:

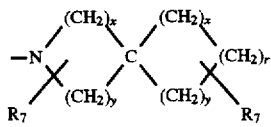

in which $R_7$, r, x and y have the meanings given above.

9) an azadicyclic group represented by:

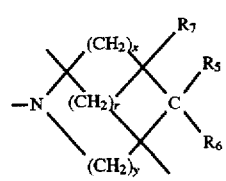

in which $R_5$, $R_6$, $R_7$, r, x and y have the meanings given above;

10) an azacycloalkyl group represented by:

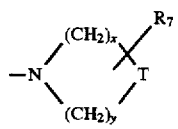

in which $R_7$, x and y have the meanings given above and T is sulphur, oxygen or $N-R_9$, where $R_9$ may be selected from H, $C_1-C_3$ alkyl or aryl, unsubstituted or mono- or di-substituted by groups selected from F, Cl, Br, $CF_3$, $NO_2$, $NH_2$, CN, $OCH_3$, and $C_1-C_3$ alkyl;

11) a linear or branched aminoalkyl group represented by:

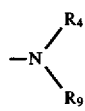

in which $R_4$ has the meaning given above and $R_9$ is a linear or branched alkyl or alkoxyalkyl group containing from 3 to 12 carbon atoms. The stereochemistry of the compounds claimed at the chiral centre marked with an asterisk in formulae (I and II) may be racetalc (D, L) or, preferably, L (laevo, sinister).

The compounds of the invention have been found to possess a considerable ability to facilitate learning and to enhance the memory of the various species studied in various experimental models in vivo.

These effects have been shown both in experimental situations in which the "basal" performance was to be increased, such as, for example, in passive-avoidance and active avoidance models in the rat, and in models in which cognitive performance was disturbed, for example, with the use of scopolamine, a drug with central anticholinergic activity, which can bring about an amnesic effect by deactivating the cholinergic neuron net or, alternatively, by inducing amnesia by cerebral electric shock.

It may be suggested that the memory- and learning-enhancing activity of the compounds of the invention may be at least partly correlated with the ability, shown in binding experiments in vitro, to interact with the receptors of the excitor amino-acids of the central nervous system (the CNS), such as the L-glutamate system.

Some of the compounds of the invention have also been found to possess considerable antidepressant activity according to an experimental model in the mouse, which is proposed as a model for evaluating the antidepressant activity of a drug.

As already mentioned, the aforesaid compounds can thus be used with advantage in the treatment and prevention of various diseases linked with deterioration or malfunctioning of the cognitive abilities such as, for example, disorders of mental performance due to mental fatigue, organic and senile cognitive deterioration, Alzheimer's disease, behavioural disorders and depressive syndromes.

The method of preparing the derivatives of the invention which are described by formula (I) and have their chiral centres in the L (laevo, sinister) form is characterized by the following steps which may be represented thus:

a) reacting the γ-benzyl ester of N-carbobenzoxy-L-glutamic acid with an amine of formula $H-R_1$, in which $R_1$ has the meaning given above, by the mixed anhydride method in an inert anhydrous solvent at a temperature of between −20° and +20° to give the compounds of formula (III) (see diagram 1);

b) debenzylating and decarbobenzoxylating the compound of formula (III) dissolved in an inert solvent in a single step by reacting it with hydrogen at ambient temperature and atmospheric pressure in the presence of catalytically effective quantities of a hydrogenation catalyst to obtain derivatives of formula (I) in which $R_2$ and $R_3$ are both hydrogen (compounds IA).

The series of steps of the method of the invention is described in its entirety in Diagram 1 below:

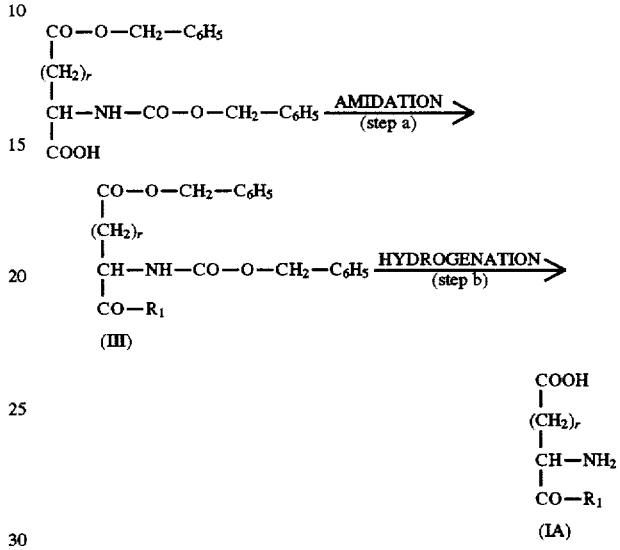

If at least one of the substitutes $R_2$ and $R_3$ as defined above is other than hydrogen, the compounds (IA) obtained as described above are alkylated by conventional techniques to give the derivatives of formula (I) in which, this time, $R_2$ and $R_3$ are selected independently from $CH_3$, $C_2H_5$, and CHO, provided that $R_2$ and $R_3$ are not simultaneously CHO.

The amidation step (a) is preferably effected at a temperature of between −10° and +5° C. for a period of from 1 to 24 hours, preferably for 6 hours, and with a stoichiometric ratio between the reagents. The preferred solvent for carrying out the reaction is selected from chloroform, dioxane and tetrahydrofuran.

The hydrogenation step (b) is preferably effected in the presence of a quantity of between 0.02 and 0.001 atoms of palladium per mole of compound (III), supported on carbon, in methanolic solution, at ambient temperature and pressure, in a stream of hydrogen, for a period of from 1 to 12 hours, preferably 6 hours.

The amines of formula $(H-R_1)$ are obtainable commercially or are prepared by conventional methods described in the literature.

The method of preparing the derivatives of formula (I) having their chiral centre in the racemic form (D, L) is similar to that described above, but starting from the corresponding γ-benzyl ester of N-carbobenzoxy-D-glutamic acid.

The method of preparing the derivatives of the invention of formula (II) in which r is 2 and $R_2$ and $R_3$ are both hydrogen is characterized by the following steps which can be represented thus (Diagram 2):

a) reacting N-carbobenzoxy-L-glutamic anhydride prepared as described by Bergmann et al (Berichte 1932, p. 1196–1197) with the appropriate amine of formula $H-R_1$, in which $R_1$ has the meaning given above, in a molar excess, preferably of 2.5:1, of amine, at a temperature of between 0° and 30° C., preferably 20° C., for a period of between 1 and 48 h, in an inert, aqueous or non-aqueous solvent such as, for example, tetrahydrofuran, dioxane, dimethylformamide, etc. The isomers of formula (IV) (see Diagram 2) can easily be separated from the isomers of formula (III) by selective extraction in a basic medium since, on average, they are more acid.

b) decarbobenzoxylating the compounds of formula (IV) as described above for the preparation of the compounds of formula (I) so as to obtain the derivatives of formula (II) in which $R_2$ and $R_3$ are both hydrogen and r=2.

The series of steps of this method for the preparation of the derivatives of formula (II-A) in which r=2 is described by the following Diagram 2:

All the intermediate compounds of formula III were synthesized with the use of the same method (see Diagram 1).

EXAMPLE 2

(Compound 23)

Preparation of 1-(4,4-dimethylcyclohexyl)-L-isoglutamine[4-amino-5-(4',4'-dimethylcyclohexylamine)-5-oxopentanoic acid (S)]. 161 g (0.335 moles) of the compound prepared according to Example 1 were dissolved in 0.7 litres of methanol and 3.5 g of 10% Pd/C suspended in water were added. Hydrogen were bubbled in at ambient temperature for 10 hours. The catalyst was filtered out and the filtered solution evaporated to dryness. The solid

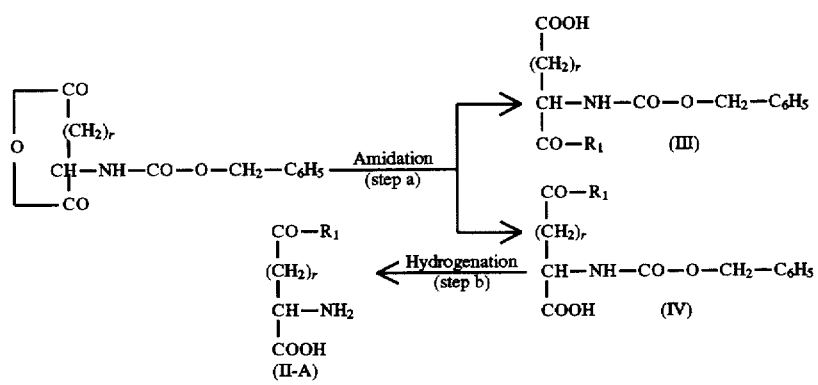

The compounds (II-A) can also be alkylated by conventional methods in this case, and give the compounds (II) as defined above.

The method for the preparation of the derivatives of formula (II) having their chiral centres in the racemic form (D, L), is similar to that described above, but starting from the corresponding N-carbobenzyloxy-DL-glutamic anhydride.

The following examples are given below to illustrate the invention further.

EXAMPLE 1

Preparation of 1-(4,4-dimethylcyclohexyl )-L-isoglutamine-N-carbobenzyloxy-5-benzylester. 100 g of L-N-carbobenzyl oxyglutamic acid-5-benzylester (0.269 moles) were dissolved in AcOEt and the solution was cooled to −5° C. 38 ml of triethylamine (0.275 moles) were added and the resulting solution was cooled to −15° C. At this temperature 26 ml of ethyl chloroformate (0.275 moles) were added dropwise. Upon completion, the mixture was left to react at −15° C. for one hour. After this period, the temperature was brought to −10° C. and a solution of 34.3 g of 4,4-dimethylcyclohexylamine (0.296 moles) in toluene was added dropwise. Upon completion of the drop addition, the mixture was left to react for one hour at −10° C. and then for one night at ambient temperature. The organic phase was washed with 2N HCl and water until the unreacted amine disappeared and then with 1N NaOH until the pH was basic. It was then washed to neutrality with water, dehydrated over sodium sulphate, the solvent was evaporated, and the oil obtained was made friable with petroleum ether. The solid obtained was filtered out and 106 g of the product were obtained.

Formula: $C_{28}H_{36}N_2O_5$ Yield 82%. TLC (BuOH/AcOH/$H_2O$ 5:2:2)$R_F$ 0.57. M.P. 72°–74° C.

obtained was taken up with acetone and stirred for one night. The product was filtered, washed with acetone, and boiled with 300 ml of water for 30 minutes. The precipitate was filtered out and washed with water and then with acetone. It was dried, giving 47.2 g of the product (Compound 23).

Formula: $C_{13}H_{24}N_2O_3$ (MW 256.35 g/mole) Yield 55%, M.P. 191°–192° C. TLC (BuOH/AcOH/$H_2O$ 5:2:2) $R_F$ 0.64. $[\alpha]_D$ =+23.2° (c=2 in MeOH).

EXAMPLE 3

(Compound 40)

Preparation of 1-(4,4-dimethylcyclohexyl)-N-formyl-L-isoglutamine. 12.8 g (0.05 moles) of compound 23 were suspended in 130 ml of formamide. The suspension was heated to 60° C. for 48 hours. The clear solution thus obtained was filtered by the addition of carbon and evaporated to dryness under vacuum. The oily residue was dissolved in ethyl acetate and washed with dilute HCl and then with $H_2O$. It was dehydrated over sodium sulphate and the solvent was evaporated, the residual oil being made friable with petroleum ether. The solid obtained was filtered and 7.1 g of the product were recovered.

Formula: $C_{14}H_{24}N_2O_4$. Yield 50%. $[\alpha]_D$=−24.6° (c=2 in MeOH) TLC (BuOH/AcOH/$H_2O$ 5:2:2) $R_F$ 0.90. M.P. 126°–128° C. EXAMPLE 4

(Compound 39)

Preparation of 1-(4,4-dimethylcyclohexyl)-N-methyl-L-isoglutamine. 5.7 g (0.02 moles) of Compound 41 were dissolved in 100 ml of tetrahydrofuran to which 0.76 g (0.02 moles) of $NaBH_4$ were added in portions, and it was checked that the temperature did not exceed 30° C. After reaction for 4 h, the mixture was hydrolized with a little $H_2O$, the solvent was evaporated, the residue was taken up with ethyl acetate and dilute HCl. The acid aqueous phase was neutralized with NaOH to pH 6.5. By cooling to a low temperature, an oily precipitate was formed and solidified with time. The solid obtained was filtered and 2.5 g of the product were recovered.

Formula $C_{14}H_{26}N_2O_3$. Yield 47%. M.P. 153°–156° C. TLC ($BuOH/AcOH/H_2O$ 5:2:2) $R_F$ 0.88. $[\alpha]_D=7.1°$ (c=2 in NaOH).

All the compounds of Formula I (See Diagram 1) were synthesized with the use of the same method. Tables A and B below give, respectively, the isoglutamines and the α-asparagines thus obtained with some identifying characteristics. For comparison purposes, some D-series enantiomers, also synthesized by the same method, have been inserted in the Tables.

TABLE A

Isoglutamine of the general formula

| Compound | R1<sup>a</sup> –R2, R3<sup>b</sup> | Stereo | Formula | $[\alpha]_o$ (NaOH) c = 2 | Melting Point (°C.) | TLC<sup>c</sup> ($R_r$) |
|---|---|---|---|---|---|---|
| 1 | butylamino | L | $C_9H_{18}N_2O_3$ | $-16.37^d$ | 142 | 0.58 |
| 2 | pentylamino | L | $C_{10}H_{20}N_2O_3$ | $+25.38^d$ | 155 | 0.62 |
| 3 | hexylamino | L | $C_{11}H_{20}N_2O_3$ | +8.85 | 146 | 0.68 |
| 4 | (3-methylbutyl)amino | L | $C_{10}H_{20}N_2O_3$ | $+22.81^d$ | 150 | 0.67 |
| 5 | (3,3-dimethylbutyl)amino | L | $C_{11}H_{22}N_2O_3$ | $+28.90^d$ | 173 | 0.62 |
| 6 | (3,3-dimethylbutyl)amino | D | $C_{11}H_{22}N_2O_3$ | $-28.50^d$ | 158 | 0.62 |
| 7 | (4,4-dimethylpentyl)amino | L | $C_{12}H_{24}N_2O_3$ | $+18.60^d$ | 139 | 0.59 |
| 8 | (3-ethylheptyl)amino | L | $C_{14}H_{28}N_2O_3$ | $+12.60^d$ | 119 | 0.65 |
| 9 | (4,6,6-trimethylheptyl)amino | L | $C_{15}H_{30}N_2O_3$ | $+10.70^d$ | 139 | 0.69 |
| 10 | (±)endo(norbornan-2-yl)amino | L | $C_{12}H_{20}N_2O_3$ | +10.59 | 182 | 0.67 |
| 11 | decahydronaphthalenyl-2-amino | L | $C_{15}H_{26}N_2O_3$ | +9.40 | 170 | 0.68 |
| 12 | (S)-1-cyclohexylethylamino | L | $C_{13}H_{24}N_2O_3$ | −2.12 | 174 | 0.74 |
| 13 | (R)-1-cyclohexylethylamino | L | $C_{13}H_{24}N_2O_3$ | +29.97 | 171 | 0.67 |
| 14 | 1-adamantylamino | L | $C_{16}H_{24}N_2O_3$ | −17.00 | 214 | 0.71 |
| 15 | 2-adamantylamino | L | $C_{15}H_{24}N_2O_3$ | $+17.20^d$ | 187 | 0.62 |
| 16 | [2-(1-adamantyl)ethyl]amino | L | $C_{17}H_{28}N_2O_3$ | $+8.60^d$ | 184 | 0.61 |
| 17 | [2-(1-adamantyl)ethyl]amino | D | $C_{17}H_{28}N_2O_3$ | −8.30 | 181 | 0.61 |
| 18 | cyclopentylamino | L | $C_{10}H_{18}N_2O_3$ | $+18.70^d$ | 170 | 0.54 |
| 19 | cyclohexylamino | L | $C_{11}H_{20}N_2O_3$ | $+26.19^d$ | 178 | 0.60 |
| 20 | cycloheptylamino | L | $C_{12}H_{22}N_2O_3$ | +15.40 | 169 | 0.61 |
| 21 | cyclooctylamino | L | $C_{13}H_{24}N_2O_3$ | +21.93 | 179 | 0.65 |
| 22 | cyclodecylamino | L | $C_{15}H_{28}N_2O_3$ | $+21.79^d$ | 160 | 0.73 |
| 23 | (4,4-dimethylcyclohexyl)amino | L | $C_{13}H_{24}N_2O_3$ | $+23.20^d$ | 192 | 0.64 |
| 24 | (4,4-dimethylcyclohexyl)amino | D | $C_{13}H_{24}N_2O_3$ | $-22.80^d$ | 186 | 0.63 |
| 25 | (4,4-dimethylcyclohexyl)amino | DL | $C_{13}H_{24}N_2O_3$ | 0 | 214 | 0.62 |
| 26 | (4,4-dimethylcyclohexyl)amino | L | $C_{15}H_{28}N_2O_3$ | +6.20 | 156 | 0.68 |
| 27 | dipropylamino | L | $C_{11}H_{22}N_2O_3$ | $+12.56^d$ | 92 | 0.61 |
| 28 | dipentylamino | L | $C_{15}H_{30}N_2O_3$ | +5.10 | 111 | 0.74 |
| 29 | decahydroisoquinolin-2-yl | L | $C_{13}H_{24}N_2O_3$ | +6.90 | 172 | 0.70 |
| 30 | 8-azaspiro[4.5]decan-8-yl | L | $C_{14}H_{24}N_2O_3$ | $+9.16^d$ | 166 | 0.60 |
| 31 | 8-azaspiro[4.5]decan-8-yl | D | $C_{14}H_{24}N_2O_3$ | −10.60 | 175 | 0.56 |
| 32 | 3-azaspiro[5.5]undecan-3-yl | L | $C_{15}H_{26}N_2O_3$ | +13.00 | 172 | 0.63 |
| 33 | 1,3,3-trimethyl-6-azadicyclo [3.2.1]octan-6-yl | L | $C_{15}H_{26}N_2O_3$ | +10.60 | 160 | 0.58 |
| 34 | heptamethylenimino | L | $C_{12}H_{22}N_2O_3$ | $-3.03^d$ | 163 | 0.55 |
| 35 | 4-morpholinyl | L | $C_9H_{16}N_2O_3$ | $+15.2^d$ | 160 | 0.33 |
| 36 | 4-methyl-1-piperazinyl | L | $C_{10}H_{19}N_2O_3$ | $+10.20^d$ | 155 | 0.24<sup>e</sup> |
| 37 | 4-phenyl-1-piperazinyl | L | $C_{15}H_{21}N_2O_3$ | +5.50 | 188 | 0.51 |
| 38 | 4-(4-chlorophenyl)-1-piperazinyl | L | $C_{15}H_{20}ClN_3O_3$ | $+5.70^d$ | 148 | 0.55 |
| 39 | (4,4-dimethylcyclohexyl)amino | L | $C_{14}H_{26}N_2O_3$ | −7.50 | 156 | 0.88 |
| 40 | (4,4-dimethylcyclohexyl)amino | L | $C_{14}H_{24}N_2O_4$ | $-24.57^d$ | 128 | 0.90 |

<sup>a</sup>in compounds 1–38 $R_2$ and $R_3$ are H;
<sup>b</sup>in Compound 39 $R_2$ is H and $R_3$ is $CH_2$. In Compound 40 $R_2$ is H and $R_3$ is C(O)H;
<sup>c</sup>BuOH/AcOH/$H_2O$ 5:2:2;
<sup>d</sup>methanol (c = 2);
<sup>e</sup>EtOH/$NH_4OH$ 9:1.

TABLE B

Asparagine (α) of the general formula

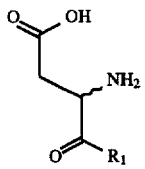

| Compound | R1 | Stereo | Formula | $[\alpha]_D$ (NaOH) c = 2 | Melting Point (°C.) | TLC[a] ($R_f$) |
|---|---|---|---|---|---|---|
| 41 | dipentylamino | L | $C_{14}H_{28}N_2O_3$ | +30.00 | 200 | 0.65 |
| 42 | dipentylamino | D | $C_{14}H_{28}N_2O_3$ | −31.70 | 206 | 0.64 |
| 43 | [2-(1-adamantyl)ethyl]amino | L | $C_{16}H_{26}N_2O_3$ | −5.60[b] | 188 | 0.62 |
| 44 | 4,4-dimethylcyclohexylamino | L | $C_{12}H_{22}N_2O_3$ | +14.60 | 219 | 0.52 |

[a] BuOH/AcOH/HO 5:2:2
[b] methanol (C = 2)

EXAMPLE 5

Preparation of 1-(4,4-dimethylcyclohexyl)-N-carbobenzyloxy-L-glutamine.

15 g (0.057 moles) of N-carbobenzyloxy-L-glutamic anhydride were dissolved in 100 ml of dimethyl formamide. The solution was cooled to 10° C. and a solution of 14.5 g of 4,4-dimethylcyclohexylamine (0.114 moles) in toluene was added dropwise. The mixture was left to react for one night at ambient temperature. The solvents were evaporated to dryness under vacuum and the residue, taken up in ethyl acetate, was washed with dilute HCl and $H_2O$. A selective extraction was then carried out with dilute NaOH with the use of 3 fractions each of 0.01 moles of NaOH. The basic aqueous phases were combined and were then acidified and re-extracted with ethyl acetate. The solvent was washed to neutrality, dehydrated over sodium sulphate and evaporated. An oily residue which did not crystallize was obtained. 8.7 g of dense oil which was pure in TLC was recovered.

TLC (isoamyl alcohol/acetone/$H_2O$ 5:2:1) $R_f$ 0.66. Formula: $C_{21}H_{30}N_2O_5$. Yield 39%.

All the intermediate compounds of formula IV were synthesized with the use of the same method (see Diagram 2).

EXAMPLE 6

(Compound 48)

Preparation of 1-(4,4-dimethylcyclohexyl )-L-glutamine.

7.8 g (0.02 moles) of the compound prepared according to Example 5 were dissolved in 100 ml of methanol to which 0.5 g of 10% Pd/C suspended in a little $H_2O$ were added. Hydrogen was bubbled in at ambient temperature for 10 hours. The catalyst was filtered out and the filtered solution evaporated to dryness. The solid obtained was taken up with acetone and stirred for one night. The product was filtered and was boiled with 30 ml of water for 30 minutes. The precipitate was filtered and washed with water and then with acetone, it was dried, producing 2.6 g of the product.

Formula: $C_{13}H_{24}N_2O_3$ (MW 256.35 g/mole) Yield 51% M.P. 217°–219° C. TLC (BuOH/AcOH/$H_2O$ 5:2:2) $R_f$ 0.51. $[\alpha]_D$=+7.2° (c=2 in $CHCl_3$).

All the compounds of formula II (see Diagram 2) in which $R_2$ and $R_3$ are both H and r is 2 were synthesized with the use of the same method.

EXAMPLE 7

(Compound 50)

Preparation of 1-(4,4-dimethylcyclohexyl)-L-(β)-asparagine.

8 g of L-aspartic acid 62 -methylester hydrochloride (0.044 moles) were suspended in 100 ml of absolute ethanol to which 16.5 g (0.13 moles) of 4,4 dimethylcyclohexylamine were added. The mixture was left to reflux for one night with stirring. The solvents were evaporated to dryness under vacuum and the residue was taken up with a little ethanol, filtered and washed with ethanol. It was crystallized with $H_2O$. 5.5 g of the product were recovered.

Formula: $C_{12}H_{22}N_2O_3$. Yield 52%. M.P. 228°–229° C. TLC (BuOH/AcOH/$H_2O$ 5:2:2) $R_f$ 0.44. $[\alpha]_D$=+8.9° (c=2 in 1N NaOH).

Table C gives the isoglutamines and the β-asparagines obtained in accordance with the foregoing examples, respectively, with some identifying characteristics. For comparison purposes, a D-series enantiomer (compound 49) was also synthesized and inserted in the Table.

TABLE C

Glutamines and Asparagines (β) of the general formula

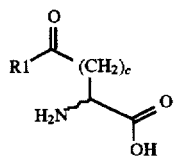

| Compound | R1[a] | Stereo | Formula | $[\alpha]_o$ (MeOH) c = 2 | Melting Point (°C.) | TLC[b] (Rf) |
|---|---|---|---|---|---|---|
| 45 | [2-(1-adamantyl)ethyl]amino | L | $C_{17}H_{28}N_2O_3$ | −6.90 | 204 | 0.64 |
| 46 | 3-azaspiro[5.5]undecan-3-yl | L | $C_{16}H_{26}N_2O_3$ | −7.11 | 173 | 0.68 |
| 47 | 1,2,3-trimethyl-6-azadicyclo [3.2.1]octan-6-yl | L | $C_{16}H_{26}N_2O_3$ | −12.24 | 175 | 0.56 |
| 48 | 4,4-dimethylcyclohexylamino | L | $C_{13}H_{24}N_2O_3$ | +7.24[d] | 219 | 0.51 |
| 49 | 4,4-dimethylcyclohexylamino | D | $C_{13}H_{24}N_2O_3$ | −7.19[d] | 221 | 0.51 |
| 50 | 4,4-dimethylcyclohexylamino | L | $C_{12}H_{22}N_2O_3$ | +8.86[d] | 229 | 0.44 |

[a]in Compounds 45–49 r is 2, in Compound 50 r is 1;
[b]BuOH/AcOH/$H_2O$ 5:2:2;
[c]chloroform (c = 2)
[d]1N NaOH (c = 2).

Description of Pharmacological Activity

1) Antiamnesic activity in the mouse (step-down passive avoidance)

A strongly aversive sensorial stimulus such as, for example, an electric shock of a suitable intensity, induces a short-term memorization of the stimulus which is subsequently transformed by means of a consolidation process, which takes from a few minutes to a few hours, into a more or less permanent memory known as a long-term memory. An electroconvulsive shock (ECS) produces retrograde amnesia in the test animal if applied immediately after the training received, for example, a harmful stimulus of a suitable intensity.

The object of the experiment was to study the effects of the compounds of the invention in antagonizing the amnesic effect of an ECS on the short-term memory consolidation process.

Method:

CD1 male mice which weighed about 30–35 g, and had not fasted were used. The equipment used was a rectangular plexiglass cage (21×21×40 cm) with an electrifiable grid floor and a wooden cube (4×4×4 cm) fixed in the centre of the cage. The animals were treated orally with the product under test 60 minutes before the training.

a) Training:

The mouse was placed delicately on the wooden cube and the time it took to descend to the grid floor (SDL=step-down latency) was measured. When all four of the animal's paws were resting on the floor the continuous 0.2 mA shock started and the time taken by The mouse to remount the wooden cube (EL=escape latency) was measured.

The animals with an SDL of between 3 and 30 sec and with an EL of between 3 and 60 sec were used for retesting.

Immediately afterwards, a transcorneal ECS was applied with the use of the following parameters: amperage 15 mA, frequency 50 Hz, duration of the train of pulses 0.4 sec. duration of each individual pulse 1 msec., interval between pulses 20 msec. As well as the groups treated with ECS, a control group without ECS and a control group with ECS were used. The amnesia thus induced was displayed in the control groups (ECS) by a reduction in the SDL in comparison with the controls without ECS.

The retest was carried out after 24 h. For this purpose, the mouse was again placed on the wooden cube and the SDL was timed (cut-off time=120 sec).

The results are expressed as the percentage variation of the SDL of the treated groups in comparison with the control group by means of this formula:

$$\% \text{ effect} = \frac{\text{treated} - \text{controls } (ECS)}{\text{controls} - \text{controls } (ECS)} \times 100$$

The compounds under test were administered in various doses in order to be able to calculate, by means of a regression line, an ID50, that is the dose in mg/kg/OS which can inhibit the amnesic effect of the ECS by 50%. The results obtained are given in Table 1 below.

TABLE 1

Antiamnesic Activity (ID50 mg/kg/OS) in the "Step Down" test in the mouse.
Amnesia induced by ECS immediately after training.
Retest 24 h. after training.
Reversal of the amnesia (% vs controls), as the increase in the "Step Down Latency"

| Compound | Dose mg/kg OS | | | | | | ID 50 (mg/kg) |
|---|---|---|---|---|---|---|---|
| | 0.1 | 0.3 | 1 | 3 | 10 | 30 | |
| 2 | — | 0 | — | 0 | — | 0 | IN[a] |
| 5 | — | 7 | — | 10 | — | 22 | NC[b] |
| 10 | 0 | — | 26 | 23 | — | — | NC |
| 11 | — | — | — | 3 | 0 | 10 | IN |
| 16 | 0 | — | 47 | 46 | 50 | 73 | 4.6 |
| 17 | 0 | — | 14 | — | 10 | — | IN |
| 19 | — | — | — | 10 | 22 | 18 | NC |
| 20 | — | — | — | 15 | 41 | 61 | 17.3 |
| 23 | 20 | — | 40 | 37 | 61 | 67 | 4.6 |
| 24 | 0 | — | 0 | — | 11 | — | IN |
| 28 | 0 | — | 0 | — | 8 | — | IN |
| 29 | — | — | — | 5 | 0 | 21 | NC |
| 32 | 7 | — | 17 | — | 10 | — | NC |
| 33 | — | — | — | 11 | 10 | 52 | 42.3 |
| 36 | — | 12 | 10 | 29 | 53 | — | 12.4 |
| 43 | — | 13 | — | 19 | — | 53 | 38.3 |
| 45 | — | — | — | 3 | 20 | 55 | 28.9 |

TABLE 1-continued

Antiamnesic Activity (ID50 mg/kg/OS) in the
"Step Down" test in the mouse.
Amnesia induced by ECS immediately after training.
Retest 24 h. after training.
Reversal of the amnesia (% vs controls),
as the increase in the "Step Down Latency"

| Compound | Dose mg/kg OS | | | | | | ID 50 (mg/kg) |
|---|---|---|---|---|---|---|---|
| | 0.1 | 0.3 | 1 | 3 | 10 | 30 | |
| Tacrine | 10 | — | 9 | 20 | 9 | — | NC |
| L-glutamic Acid* | — | — | 0 | — | 0 | 0(*) | IN |
| L-glutamine* | — | — | 0 | — | 10 | 12(*) | IN |

*IN = INACTIVE
ᵇNC = NOT CALBULABLE
(*)Dose 100 mg/kg

In this test, the antiamnesic activity was particularly remarkable for the isoglutamines of formula (I) in which $R_2$ and $R_3$ are H and in which $R_1$ is the [2-(1-adamantyl)ethyl] amino group (Compound 16), the (4,4-dimethylcyclohexyl) amino group (Compound 23), or the 4,4-methyl-1-piperazinyl group (Compound 36).

It is interesting to note that the corresponding glutamines (Compounds of formula II) were less active (for example, the compound 45), as were the corresponding -asparagines (Compound 43). The corresponding D-isoglutamines which were synthesized and tabulated for comparative purposes (see, for example, Compounds 17 and 24) were completely inactive.

The "parent compounds" L-glutamic acid and L-glutamine, which were tested up to a dose of 100 mg/kg were also inactive in this model as was tacrine, an anticholinesterase drug suggested for the treatment of senile dementia. The activity of some of the compounds of the invention seems even more remarkable if account is taken of their low toxicity. Thus, for example, Compound 23 has an LD50 in the mouse of 290 mg/kg/IV and 1300 mg/kg/OS.

2) Memory-enhancement activity in the "passive avoidance" test in the rat

A "passive avoidance" model was used, which required a single "step-through" situation and a retest of the "retention memory" 72 h after the training.

Male Wistar rats which weighed about 200 g and had not fasted, were used. The test consisted of evaluating the degree of memory of an animal after it had been trained as follows.

The equipment used was a shuttle box modified thus: one compartment was lined with black card including the cover, and a 60 W lamp was disposed above the other, spaced from the grid floor by about 40 cm. The two compartments were divided by an automatic guillotine-like door. Each animal was placed in the compartment in the light with the guillotine-like door open. From this moment, the time taken by the rat to go into the compartment lined with black card (the dark compartment) (the step-through latency=STL) was measured. The animals which took more than 30 sec to go into the dark were discarded. Once they had gone into the dark, the door was lowered automatically and a=0.1 mA shock lasting 5 sec (a foot shock=FS) started. After 10 sec, the animal was removed from the shuttle box.

Upon completion, the animals were selected randomly in homogeneous groups and treated with the products.

The retest to determine memory was made after 72 hours. The products were administered chronically in the preselected manner twice per day and the last treatment 30 min before the retest (6 treatments altogether).

The memory-retention test (the retest) consisted of placing each animal, treated 30 min beforehand with a physiological solution or with the product, in the compartment which was not lined with black card for 30 sec. After this, the light was switched on and, after 5 sec, the door was raised and the time taken to go into the dark was measured up to a maximum time of 120 sec (the cut-off time).

The animal, which remembered that it received the shock in the dark, did not move from the intense light even though this was an aversive stimulus. This is the reason for the term used to define the test, that is, passive avoidance=the animal does not have to take any action to avoid punishment. The results are expressed as the percentage variation of the STL (in seconds) of the groups treated in comparison with the control group by means of this formula:

$$\% \text{ effect} = \frac{\text{treated} - \text{controls}}{120 - \text{controls}} \times 100$$

The compounds under test were administered in various doses in order to be able to calculate, by means of a regression line, an ED30, that is, the dose in mg/kg IP which could increase the latency time (STL) by 30% in comparison with the untreated controls. The results are given in Table 2 below.

From the data recorded, it can be noted that some compounds of the invention, such as Compounds 16, 20 and 23, have considerable activity in increasing the avoidance time in comparison with the untreated controls in the retest on the 4th day after the training. The corresponding D-series derivatives (such as, for example, Compounds 17 and 24) were also inactive in this case, as were the comparison compounds used, that is, tacrine and piracetam, a drug described as nootropic (Martindale, 1989, p. 1602).

TABLE 2

Passive avoidance in the rat.
Foot shock (FS) 0.1 mA; Retest on the
4th day after training (6 treatments).
% variation vs controls (FS)
in "step through latency"

| Compound | Dose mg/kg IP | | | ED30 mg/kg (IP) |
|---|---|---|---|---|
| | 0.1 | 1 | 10 | |
| 16 | 11 | 21 | 57 | 1.0 |
| 17 | 0 | 0 | 0 | IN* |
| 20 | 7 | 20 | 36 | 4.2 |
| 23 | 11 | 19 | 43 | 2.3 |
| 24 | 8 | 0 | 0 | IN |
| 32 | 0 | 14 | 15 | NCᵇ |
| 43 | 10 | 16 | 29 | 16.9 |
| 45 | 0 | 0 | 12 | NC |
| 48 | 6 | 0 | 18 | NC |
| Piracetam (*) | 0 | 0 | 0 | IN |
| Tacrine | 7 | 6 | 12 | NC |

*IN = INACTIVE
ᵇNC = NOT CALCULABLE
(*)Doses: 3-10-30 mg/kg

3) Memory-enhancement activity in the "active avoidance" test in the rat

Male Wistar rats which weighed about 200 g and had not fasted were used. The method consisted of making the animal understand that, in order to avoid a shock, it must go from one compartment of the equipment used (a shuttle box) to the other. For this reason it is defined as active avoidance (because the animal takes action to avoid the punishment).

It therefore differs from the passive avoidance test in which the animal does not have to take any action to avoid punishment.

In this test it is also possible to discriminate between two different parameters: memory and learning.

The equipment consisted of a cage divided into two portions by a wall with an opening at floor level to enable the animal to go from one portion of the cage to the other.

The cage had a lamp disposed on its cover for giving the light stimulus which, together with the sound stimulus constituted two stimuli (conditioners) for the conditioning of the animal.

The reinforcement, that is, the reason which forced the rat to become conditioned to the sound and to the light, consisted of an electrical stimulus coming from the grid floor of the cage (an Unconditioned stimulus). The floor of the cage was constituted by a metal grid for the passage of the current and could rock so that, each time the rat passed through the dividing hole, the floor tilted, due to its weight, interrupting the current.

The test lasted for five days. On the first day, the animals were subjected to the first session of 40 cycles with an interval of 30 sec between cycles (duration of the session=20 minutes).

For each 30 sec cycle, a light stimulus and a sound stimulus lasting for 3 seconds were applied, followed by the 0.4 mA shock, which also lasted for 3 sec.

If the rat went into the other compartment within the first 3 sec during the conditioning stimuli (light and sound) it did not receive a shock and the response was defined as an avoidance response.

If not, it received a shock and two evaluation parameters were distinguished: the escape response if it received only a portion of the shock, and the shock response if it did not move from the compartment and underwent the shock throughout its duration.

At the end of the first day, the rats were selected randomly in homogeneous groups and treated with the product under test or with physiological solutions (controls).

On subsequent days, the rats underwent the first treatment 15 minutes before the session and the second treatment at the end of the day. In 5 days of tests the animal thus underwent 8 treatments in total.

The 40 cycles were divided into 4 sessions each of 10 cycles for the 5 days' duration of the test.

The performance of each animal was evaluated as: % shock response, % escape response; % total avoidance response (these refer to all 40 cycles of each day); memory, as % of the avoidance responses in the first session of each day (the first 10 cycles); learning: as % of avoidance responses in the fourth session of each day (the last 10 cycles).

All the % were calculated on regression lines calculated on the basis of the responses obtained daily for each individual parameter, on the fifth (last) day of the experiment.

The results are expressed as the percentage variation of the averages of the individual responses obtained for the treated groups in comparison with the control group. The results thus calculated are given in Table 3 below, which gives the statistical analysis between the treatment groups against the controls, carried out by analysis of the relative variance with respect to the overall results for the 5 days.

It can be seen from the results shown in the table that Compound 23 significantly increases the total avoidance responses in a dose-dependent manner whilst the shock responses are greatly reduced.

The compounds seems to be equally effective in enhancing both memory (% avoidance in the first 10 trials) and learning (% avoidance in the last 10 trials of each session).

TABLE 3

Active Avoidance in the Rat
SITUATION ON THE FIFTH DAY CALCULATED ON REGRESSION LINES

| TREATMENT (I.P.) | DOSE (MG/KG) 2/DAY | AVERAGE % SHOCK RESPONSE | AVERAGE % ESCAPE RESPONSE | AVERAGE % TOT.AVOID RESPONSE 40 TRIALS (TR) | AVERAGE % AVOIDANCE MEMORY FIRST 10 TR/40 TR | AVERAGE % AVOIDANCE LEARNING LAST 10 TR/10 TR |
|---|---|---|---|---|---|---|
| CONTROLS | | 70 | 9 | 21 | 12 | 29 |
| COMPOUND 23 | 1 | 64 | 8 | 26 | 10 | 34 |
| " | 3 | 34 | 22 | 44 | 29 | 53 |
| " | 10 | 13 | 31 | 56 | 34 | 71 |
| % VARIAT. VS CONTROLS | | | | | | |
| COMPOUND 23 | 1 | −8.6 * | −11.1 * | +33.3 ** | −16.7 ** | +17.2 * |
| " | 3 | −51.4 *** | +144 ** | +109 ** | +142 *** | +82.7 ** |
| " | 10 | −81.4 | +241 | +166 | +183 | +145 |

* P < 0.05
** P < 0.01
*** P < 0.001

4) Antagonism of the amnesic effect induced by scopolamine in the "passive avoidance" test in the rat.

It has been found that acetylcholine is a neurotransmitter which performs an important role in learning and memory processes. The manipulation of the central cholinergic system can therefore bring about significant changes in the performance of the animals studied in the various experimental models adopted.

In fact it has been found, for example (Heiese G. A., Med. Res. Rev. 4 (1984), 535–538) that scopolamine and other cholinolytics worsen performance in various cognitive models.

It was therefore desired to test if Compound 23, that is, one of the compounds which was found most active in the models described above, could antagonize the activity of a cerebral muscarinic antagonist such as scopolamine on learning and memory processes.

The shuttle box equipment was used for passive avoidance as described in Experiment 2 with the following modifications: the compounds (or physiological solutions for the control group) were administered intraperitoneally (IP) 45 min before the training, whereas scopolamine (SCOP) was administered 30 min before the training. The foot shock (FS) consisted of a 0.2 mA shock of 5 sec duration.

The retest to determine memory was executed 24 h after the training. In each individual experiment, the following groups were used: a control group (−FS), a control group (+FS), a control group (FS+SCOP), 3 treatment groups with different doses of the product under test (FS+SCOP).

The results obtained are expressed as the percentage variation of the step-through latencies (STL) (in seconds) of the groups treated in comparison with the control group, by means of the following formula:

$$\% \text{ effect} = \frac{\text{treated} - \text{controls }(FS + SCOP)}{\text{controls }(FS) - \text{controls }(FS - SCOP)}$$

An ID50, that is, the dose in mg/kg IP which could antagonize the amnesic effect of scopolamine by 50% was then calcuated by regression. The results obtained for the Compound 23 tested in comparison with tacrine are given in Table 4 below.

It can be seen from the results given that Compound 23 antagonizes the amnesic effect induced by scopolamine in a dose-dependent manner. Its activity is comparable, in this model, with that of tacrine, although Compound 23 is not a drug with cholinomimetic action.

At time 0, each animal was immersed in a beaker and, after one minute during which all moved about swimming vigorously in order to escape, regardless of treatment, the observer, who was unaware of the treatment, assigned the following points:

0=animal immobile

1=minimum movement to remain afloat

2=vigorous swimming

The greater the antidepressant activity of the drug, the more the animals will move about in order to try to escape from the water.

The points were assigned every 15 sec for a total period of 5 min with a total of 20 observations. The antidepressant activity was determined with the use of various doses of the compound by the regression method as the ED50, that is, the dose in mg/kg of the compound which could antagonise the animal's immobility time by 50%.

The results obtained for some of the compounds of the invention are set out in Table 5 below.

It can be seen from the data obtained that some of the compounds of the invention, such as, for example, Compounds 16, 23 and 43, have an antidepressant effect of the same order of magnitude as the comparison drug used, amitriptyline, a tricyclic antidepressant with great pharmacological potency. The corresponding D-series derivatives, such as Compounds 17 and 24, were also inactive in this test.

TABLE 4

Passive avoidance in the rat
Anti-scopolamine activity
Foot shock (FS) 0.2 mA; Retest 24 h after training

|  | Dose mg/kg IP | Latency (STL)* (sec) | % Effect controls vs | ID 50 |
|---|---|---|---|---|
| CONTROL (FS) | — | 94.7 | — |  |
| CONTROL (FS + SCOP)(**) | — | 58.2 | — |  |
| COMPOUND 23 (FS + SCOP) | 0.1 | 60.8 | 7.1 | 4.7 mg/kg |
| " | 1 | 72.0 | 38.0 |  |
| " | 10 | 78.6 | 55.8 |  |
| CONTROL (FS) | — | 89.0 | — |  |
| CONTROL (FS + SCOP) | — | 62.0 | — |  |
| TACRINE (FS + SCOP) | 0.3 | 59.7 | 0 | 3.4 mg.kg |
| " | 1 | 73.1 | 41.1 |  |
| " | 3 | 75.3 | 49.2 |  |
| " | 10 | 79.5 | 64.8 |  |

*STL: Step Through Latency
(**)SCOP: SCOPOLAMINE

5) Antidepressant activity in the "behavioural despair test"

Another interesting aspect of the pharmacological activity of these products is the potent antidepressant activity which some of them display in an experimental model in the mouse, in which a state of depression is induced experimentally by the method of Porsolt et al. (Arch. Int. Pharmacodyn. 229, p. 327–336 (1977)).

Method:

Male CD1 mice which weighed about 20–25 g and had not fasted were used. The test consisted of inducing a state of depression in the animal which was subjected to forced swimming in a glass cylinder from which it could not escape.

After a short period of vigorous activity the mouse adopted a characteristic posture of immobility which was easily identifiable; this immobility is reduced by antidepressant drugs. 1 l glass beakers, filled to 700 ml with water at a temperature of 25° C. were used for the test.

The mice, 8 per group, were treated intraperitoneally with the drug under test, 30 minutes before the test.

TABLE 5

Antidepressive activity (ED50 mg/kg IP) in the
"behavioural despair test" in the mouse.
Decrease in immobility (as %) vs the controls during the
5 minutes' duration of the experiment

| Compound | Dose mg/kg IP | | | | ED50 (mg/kg) |
|---|---|---|---|---|---|
|  | 1 | 3 | 10 | 30 |  |
| 5 | — | 12 | 32 | 23 | Not Calculable |
| 7 | — | 19 | 51 | 67 | 12.3 |
| 11 | 5 | 32 | 64 | 19 | 13.5 |
| 14 | — | 0 | 0 | 21 | Inactive |
| 15 | — | 0 | 33 | 75 | 15.4 |
| 16 | 15 | 46 | 77 | 98 | 3.9 |
| 17 | — | 7 | 12 | 0 | Inactive |
| 20 | — | 0 | 11 | 52 | 36.1 |
| 23 | — | 14 | 31 | 94 | 11.1 |
| 24 | — | 0 | 16 | 19 | Inactive |

TABLE 5-continued

Antidepressive activity (ED50 mg/kg IP) in the
"behavioural despair test" in the mouse.
Decrease in immobility (as %) vs the controls during the
5 minutes' duration of the experiment

| Compound | Dose mg/kg IP | | | | ED50 (mg/kg) |
|---|---|---|---|---|---|
| | 1 | 3 | 10 | 30 | |
| 26 | — | 15 | 30 | 46 | 43.0 |
| 30 | — | 0 | 25 | 20 | Not Calculable |
| 43 | 0 | 34 | 60 | 93 | 6.4 |
| 48 | 0 | 9 | 18 | 38 | Not Calculable |
| Amitriptyline | 19 | 20 | 88 | — | 4.1 |

6) Studies on binding to rat "forebrain" membranes

It has been suggested that glutamate, asparzate and other possible excitor amino-acids function as neurontransmitters in the majority of the excitatory synapses of the CNS of vertebrates and may therefore be implicated in the learning and memory processes. The synaptic responses elicited by the excitor amino-acids are mediated by at least three different receptor subtypes, known as quisqualate (or AMPA), N-methyl-D-aspartate (NMDA), and kainate.

L-glutamate recognizes all three receptor subtypes indicated above, al though not selectively. It is therefore desirable to evaluate the capacity of each of the compounds of the invention to interact with the excitor amino-acid receptors of the CNS.

"Forebrain", that is, the cerebral cortex and the hippocampus, were selected as the receptor tissue and $^3$H-L-glutamate as the ligand for marking this heterogenous receptor population.

Rat cerebral tissue (forebrain without striated tissue) was therefore homogeneised cold in tris buffer at pH 7.4. After washing and centrifuging, the final pellet was resuspended in 50 volumes of tris HCl binding buffer at 7.1. 0.5 ml of receptor membrane thus obtained were then incubated, together with the radioactive tracer and the compounds under test, for 20 min at 37° C. The reaction was terminated by separating the bound radio-ligand from the free radio-ligand by filteration on glass-fibre filters which, after washing, were counted in a liquid scintillator (a β-counter) thus determining the radioactivity associated with the pellet. The specific binding was determined as the difference between the binding in the absence and in the presence of cold 3.6 mM L-glutamate.

The results thus obtained are shown in Table 6, in which the IC50 of the compounds tested, that is, the concentration (in μmoles/litre) of the antagonist which could displace 50% of the ($^3$H-L-glutamate) ligand from the receptor are given. It can be seen from the data given in Table 6 that some of the compounds of the invention, such as, for example, Compounds 16, 20 and 23, have considerable activity in inhibiting the binding of the glutamate to the receptors of cortical membranes of rats. The most active compounds were in fact only about 10 times less active than the specific antagonist (L-glutamate). The derivatives belonging to the R series were practically inactive.

As already mentioned, the ability to interact with the cortical receptors of the excitor amino-acids such as L-glutamate, may at least partially be interpreted as one of the mechanisms by which the compounds of the invention enhance memory and learning in the animals of the various experimental models used. The inactivity of exogenous glutamic acid in these models could result from its inability to overcome the blood-brain barrier, being too polar a compound and hence not sufficiently bio-available to be able to carry out any pharmacological activity at the level of the CNS in vivo.

TABLE 6

Inhibition of the specific binding of
[$^3$H]-glutamate to the cortical membranes
("forebrain") of rats in comparison with
the reference excitor amino-acids.

| COMPOUND | IC50 (μmoles/liter) |
|---|---|
| 1 | 72.0 |
| 2 | 74.6 |
| 3 | 70.0 |
| 5 | 20.1 |
| 6 | IN(*) |
| 7 | 194.3 |
| 8 | 56.4 |
| 10 | 16.0 |
| 11 | 35.7 |
| 12 | 168.6 |
| 13 | 54.0 |
| 14 | 73.3 |
| 15 | 132.0 |
| 16 | 15.0 |
| 17 | 312.1 |
| 18 | 21.2 |
| 19 | 17.2 |
| 20 | 14.4 |
| 22 | 64.0 |
| 23 | 13.8 |
| 24 | IN |
| 26 | 36.3 |
| 27 | 970.0 |
| 29 | 28.6 |
| 30 | 368.0 |
| 33 | 202.8 |
| 34 | 165.6 |
| 35 | 29.2 |
| 39 | 18.8 |
| 41 | 136.2 |
| 43 | 33.5 |
| 44 | 38.6 |
| 45 | 61.2 |
| 47 | 55.9 |
| 48 | 70.7 |
| 49 | IN |
| 50 | 100.7 |
| L-glutamic acid | 1.6 |
| D-glutamic acid | 1039.0 |
| L-aspartic acid | 30.0 |

(*)IN = INACTIVE (>1mM)

We claim:

1. A compound represented by general formula (I) below, or a pharmaceutically acceptable salt thereof:

wherein r is 2, $R_2$ and $R_3$ are each selected from the group consisting of H, $CH_3$, $C_2H_5$ and CHO, provided that $R_2$ and $R_3$ are not simultaneously CHO, and wherein $R_1$ is selected from the group consisting of:

(a) an aminoalkladamantyl group represented by:

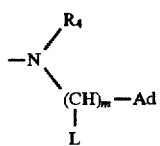

wherein $R_4$ is selected from the group consisting of H, $C_1$–$C_5$ alkyl and $C_1$–$C_5$ alkoxyalkyl, m is 0 or an integer of 1 to 3, L is selected from the group consisting of H, $C_1$–$C_3$ alkyl and $C_1$–$C_3$ alkoxyalkyl, and Ad is adamantyl (1- or 2-yl), (b) a monocyclic animoalkyl group represented by:

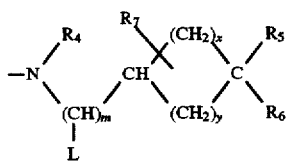

wherein $R_4$, m and L each have the meanings given above, x and y are each independently an integer of 1 to 4, provided that the ring formed comprises between 5 and 10 carbon atoms, and wherein $R_5$, $R_6$ and $R_7$ are each selected from the group consisting of H, $C_1$–$C_4$ alkyl and $C_1$–$C_4$ alkoxyalkyl group, provided that $R_5$ and $R_6$ are not simultaneously H, (c) a dicyclic aminospiro group represented by:

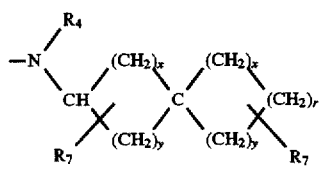

wherein $R_4$, $R_7$, r, x and y each have the meanings given above, (d) a dicyclic amino group (orthofused) represented by:

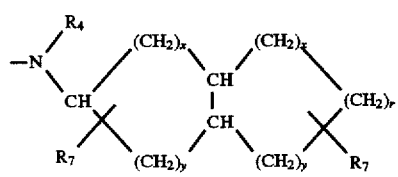

wherein $R_4$, $R_7$, r, x and y each have the meanings given above, and (e) a dicyclic amino group represented by:

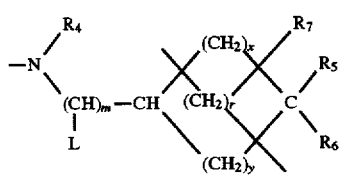

wherein $R_4$, $R_5$, $R_6$, $R_7$, L, m, r, x and y each have the meanings given above,
wherein the stereochemistry of the compound at the chiral center, which is marked with an asterisk in formula (I), is L (laevo, sinister).

2. The compound according to claims 1, wherein the chiral center is in the L (laevo) form, wherein $R_2$ and $R_3$ are each H, and wherein $R_1$ is selected from the group consisting of:

(a) an aminoalkyladamantyl group represented by:

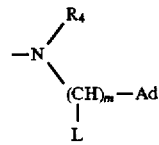

wherein $R_4$ is H or $CH_3$, m is 0 or an integer of 1 to 2, L is H or $CH_3$ and Ad is adamantyl (1- or 2-yl), (b) a monocyclic aminoalkyl group represented by:

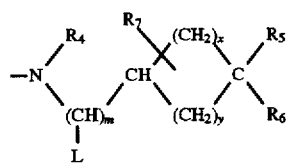

wherein $R_4$, m and L each have the meanings given above, x and y are each independently an integer of 1 to 3, provided that the ring formed comprises between 5 and 8 carbon atoms, and wherein $R_5$, $R_6$ and $R_7$ are each independently H or $CH_3$, (c) a dicyclic aminospiro group represented by:

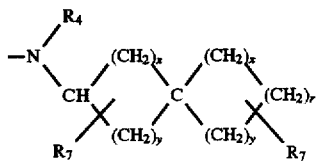

wherein $R_4$, $R_7$, r, x and y each have the meanings given above, (d) a dicyclic amino group (orthofused) represented by:

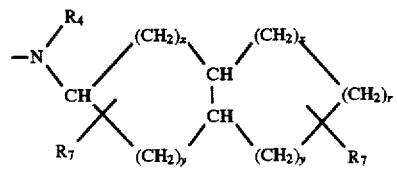

wherein $R_4$, $R_7$, r, x and y each have the meanings given above, and (e) an aminodicyclic group represented by:

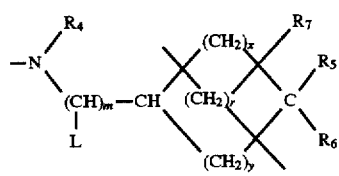

wherein $R_4$, $R_5$, $R_6$, $R_7$, L, m, r, x and y each have the meanings given above.

3. The compound according to claim 2, wherein $R_1$ is selected from the group consisting of:

(a) an aminoalkyladamantyl group represented by:

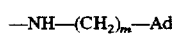

wherein m is 0 or an integer of 1 to 2, and Ad is adamantyl (1- or 2-yl), (b) a monocyclic aminoalkyl group represented by:

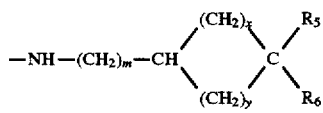

wherein m has the meaning given above, x and y are each independently an integer of 1 to 3, provided the ring formed comprises between 5 and 8 carbon atoms, and wherein $R_5$ and $R_6$ are each independently H or $CH_3$.

4. A pharmaceutical preparation comprising, as an active substance, at least one compound according to claim 1 or a pharmaceutically acceptable salt thereof, and a pharmaceutically acceptable carrier.

5. The pharmaceutical preparation according to claim 4, wherein said preparation further comprises a pharmaceutically acceptable inactive ingredient selected from the group consisting of a vehicle, a binder, a flavoring, a dispersant, a preservative, a humectant and mixtures thereof.

6. A method for the prevention and treatment of diseases linked to a deterioration or malfunctioning of the cognitive powders or for enhancing learning and memory comprising administering to a subject in need of such prevention or treatment, the pharmaceutical preparation of claim 4.

7. A method for treatment of disorders of mental performance due to mental fatigue or to organic deterioration comprising administering to a subject in need of such treatment, the pharmaceutical preparation of claim 4.

8. A method for treatment of various pathological conditions of the central nervous system comprising administering to a subject in need of such treatment, the pharmaceutical preparation of claim 4.

9. A method for treatment of presenile and senile dementia comprising administering to a subject in need of such treatment, a pharmaceutically effective amount of the pharmaceutical preparation of claim 4.

10. A method for preparing a compound of formula (I) according to claim 1, wherein r, $R_1$, $R_2$ and $R_3$ have the meanings given in claim 1, and wherein the substituents at the chiral center, marked with an asterisk in formula (I), have the (L) or (D, L) conformation, comprising the following stereo-conservative steps:

(a) reacting γ-benzylester or N-carbobenzoxy-L-(or D, L)-glutamic acid, according to the mixed anhydride method, with an amine of formula $H-R_1$, wherein $R_1$ has the meaning given above, with the proviso that at least one of $R_2$ and $R_3$ is other than H, at a temperature of from −20° C. to +20° C. and in an inert anhydrous solvent, and recovering a compound of formula (III) from the reaction mass:

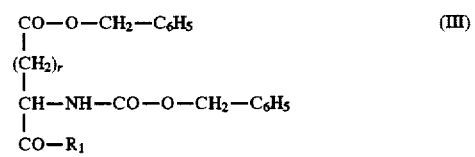

(b) debenzylating and decarbobenzoxylating the compound of formula (III), dissolved in an inert solvent, by reacting it at ambient temperature and pressure with hydrogen in the presence of a catalytically effective amount of a hydrogenation catalyst, and recovering a compound of formula (IA) from the reaction mass:

(c) alkylating the compound of formula (IA) to give the compound of formula (I), wherein $R_2$ and $R_3$ are each selected from the group consisting of $CH_3$, $C_2H_3$ and CHO, provided that $R_2$ and $R_3$ are not simultaneously CHO.

11. A compound represented by general formula (I) below, or a pharmaceutically acceptable salt thereof:

wherein r is 2, $R_2$ and $R_3$ are each selected from the group consisting of H, $CH_3$, $C_2H_5$ and CHO, provided that $R_2$ and $R_3$ are not simultaneously CHO, and wherein $R_1$ is a monocyclic animoalkyl group represented by:

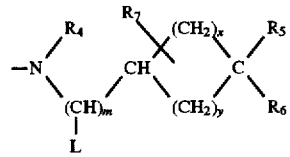

wherein $R_4$, m and L each have the meanings given above, x and y are each independently an integer of 1 to 4, provided that the ring formed comprises between 5 and 10 carbon atoms, and wherein $R_5$, $R_6$ and $R_7$ are each selected from the group consisting of H, $C_1$–$C_4$ alkyl and $C_1$–$C_4$ alkoxyalkyl group, provided that $R_5$ and $R_6$ are not simultaneously H, wherein the stereochemistry of the compound at the chiral center, which is marked with an asterisk in formula (I), is racemic (D, L) or L (laevo, sinister).

* * * * *